(12) United States Patent
Boyd

(10) Patent No.: US 8,549,898 B2
(45) Date of Patent: Oct. 8, 2013

(54) FLUID MONITORING APPARATUS AND A METHOD OF OPERATING THE SAME

(75) Inventor: Nathan Boyd, Manchester (GB)

(73) Assignee: Intelisys Limited, Manchester (GB)

( * ) Notice: Subject to any disclaimer, the term of this patent is extended or adjusted under 35 U.S.C. 154(b) by 707 days.

(21) Appl. No.: 12/445,503

(22) PCT Filed: Oct. 12, 2007

(86) PCT No.: PCT/GB2007/050632
§ 371 (c)(1),
(2), (4) Date: Jan. 27, 2010

(87) PCT Pub. No.: WO2008/047159
PCT Pub. Date: Apr. 24, 2008

(65) Prior Publication Data
US 2010/0132440 A1    Jun. 3, 2010

(30) Foreign Application Priority Data
Oct. 18, 2006 (GB) .................................. 0620691.6

(51) Int. Cl.
*G01N 1/40* (2006.01)

(52) U.S. Cl.
USPC ........................................... 73/64.56

(58) Field of Classification Search
USPC ........ 73/64.56, 863, 863.71, 863.81; 324/693
See application file for complete search history.

(56) References Cited

U.S. PATENT DOCUMENTS

| 5,864,140 A | 1/1999 | Owens ............................ 172/61 |
| 6,221,257 B1 * | 4/2001 | Grim ........................... 210/747.1 |
| 7,250,302 B2 * | 7/2007 | Bernhardsson et al. ......... 436/49 |
| 2007/0163334 A1 | 7/2007 | Boyd ........................... 73/64.56 |

FOREIGN PATENT DOCUMENTS

| EP | 0065166 A2 | 11/1982 |
| FR | 2708347 A1 | 2/1995 |
| JP | 07286339 A2 | 10/1995 |
| JP | 2000146889 A2 | 5/2000 |
| WO | 0109041 A3 | 2/2001 |

* cited by examiner

*Primary Examiner* — Peter Macchiarolo
*Assistant Examiner* — Tamiko Bellamy
(74) *Attorney, Agent, or Firm* — Trego, Hines & Ladenheim, PLLC

(57) ABSTRACT

A sampling apparatus for sampling a fluid, the apparatus comprising a sensor and a flow regulator open to allow the continuous flow of fluid through the apparatus past the sensor.

21 Claims, 6 Drawing Sheets

FLUID MONITORING APPARATUS AND A METHOD OF OPERATING THE SAME

FIELD OF THE INVENTION

The present invention relates to sampling apparatus and to methods of operating the same.

BACKGROUND TO THE INVENTION

In order to monitor water quality in mains supplies intended for consumption, i.e. drinking water, it is necessary to sample the water supply from time to time. Currently this is usually achieved by a technician visiting a hydrant, accessing the water supply and carrying out suitable tests with portable sampling equipment that is taken from job to job. Alternatively, the water main may be exposed by excavation and then drilled into and an insertion valve fitted, through which an instrument may be attached to the main. These methods are so time consuming and expensive as to make extensive monitoring impractical.

WO-A-2005/052573 discloses a sampling apparatus attachable to a hydrant (these provide extensive access to the mains distribution network) with an outlet configured to provide periodic flows of fluid through the apparatus. However, it is desirable to have a less complex apparatus and certain water quality sensors cannot function adequately in a periodic flow.

SUMMARY OF THE INVENTION

According to the present invention in a first aspect, there is provided a sampling apparatus for sampling a fluid, the apparatus comprising a sensor and a flow regulator open to allow the continuous flow of fluid though the apparatus past the sensor, wherein the fluid ejector is configured to direct fluid at the sensor at an incident angle of from 30° to 60°.

Suitably, the apparatus is attachable to a hydrant. Suitably, the apparatus comprises a hydrant connector for connecting the apparatus to a hydrant, which hydrant connector comprises a threaded cap.

Suitably, the sensor is configured to periodically make a reading of a characteristic of the fluid. Suitably, the reading is stored in a memory. Suitably, the apparatus comprises a connector for data download to an external device, such as a personal digital assistant (PDA). Suitably, the apparatus further comprises a transmitter for the wireless transmission of data to an external device. Suitably, the transmitter is an antenna.

Suitably, the sensor is selected from one of a chlorine sensor, a pH sensor and an electrical conductivity sensor. Suitably, the apparatus comprises a plurality of sensors selected from one or more of a chlorine sensor, a pH sensor and an electrical conductivity sensor.

Suitably, the apparatus comprises a fluid flow path for fluid through the apparatus and a non-return valve in the fluid flow path.

Suitably, the flow regulator reduces the pressure of the fluid flow. This enables the water pressure to be reduced to a pressure suitable for the sensor, which generally is from 10-16 bar mains pressure to less than 1 bar and preferably about 0.1 bar.

Suitably, the apparatus further comprises a fluid ejector configured to direct fluid at the sensor.

Suitably, the fluid ejector is configured to direct fluid at the sensor at an incident angle from 40° to 50°. This helps ensure that bubbles and particulates do not build up on the sensor.

Suitably, the sensor is a membrane sensor.

The flow rate of the fluid need not be constant, though it is desirable if it is. Suitably, the flow rate through the apparatus is in the range 0.05 liters per minute to 3 liters per minute. More suitably, the flow range is from 0.05 liters per minute to 1 liter pre minute. More suitably still, the flow rate is in the range 0.075 liters per minute to 0.5 liters per minute. Preferably, the flow rate is in the range 0.09 liters per minute to 0.15 liters per minute. The most preferred flow rate is 0.1 liters per minute.

Suitably, the fluid is a liquid. Suitably, the liquid is water.

Suitably, the apparatus is for sampling water in a water distribution network.

Suitably, the apparatus is configured whereby the water pressure is from the mains supply.

According to the present invention in a second aspect, there is provided a method of operating an apparatus according to the first aspect of the invention, which method comprises, when the apparatus is attached to a fluid supply configuring the flow regulator to all the continuous flow of fluid through the apparatus.

BRIEF DESCRIPTION OF THE DRAWINGS

The present invention will now be described, by way of example only, with reference to the accompanying drawings; in which.

DESCRIPTION OF THE PREFERRED EMBODIMENTS

Figure 1:
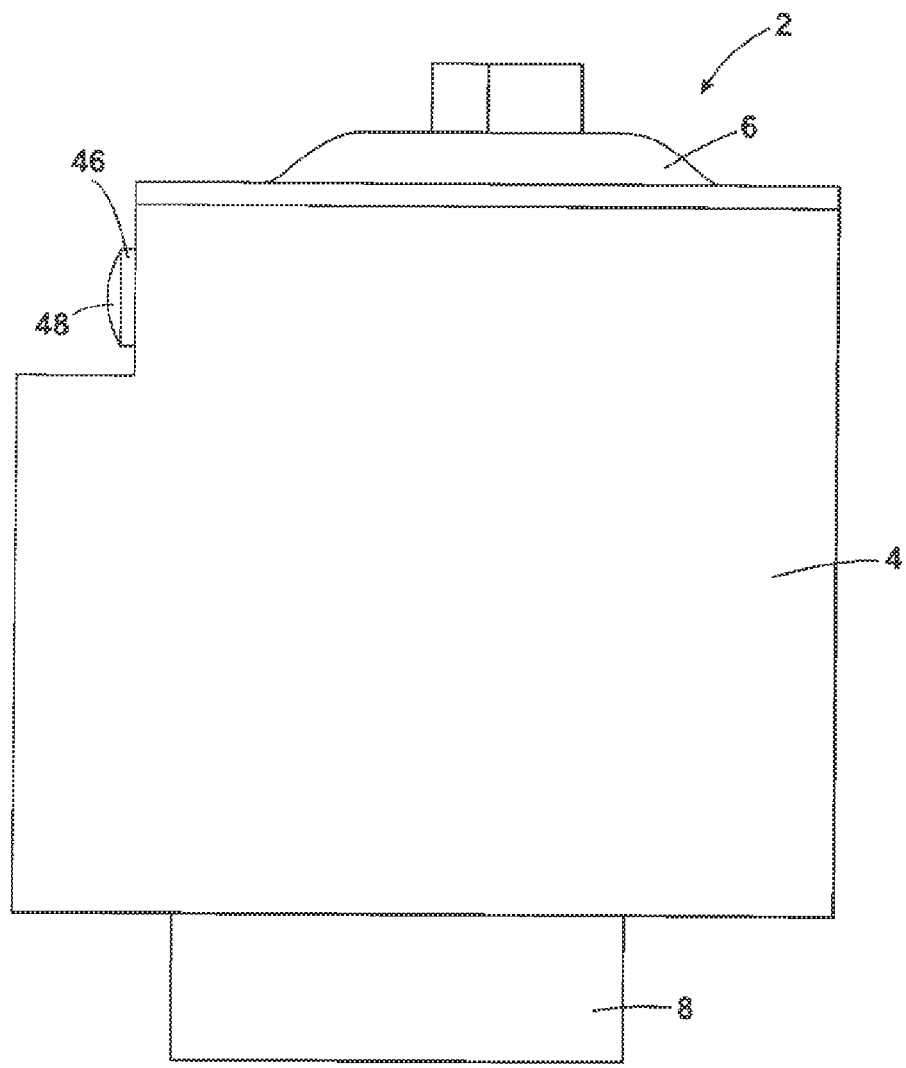
FIG. 1 is a front view of a sampling apparatus according to a first embodiment the present invention.

Referring to FIG. 1 of the accompanying drawings, there is shown a sampling apparatus 2 according to the present invention. The sampling apparatus comprises a main body 4, a lid 6 and a hydrant connector 8. The main body 4 and hydrant connector 8 are formed from aluminium alloy. The lid 6 is bolted onto the main body 4 and is made of a tough plastic e.g. polycarbonate.

Figure 2:
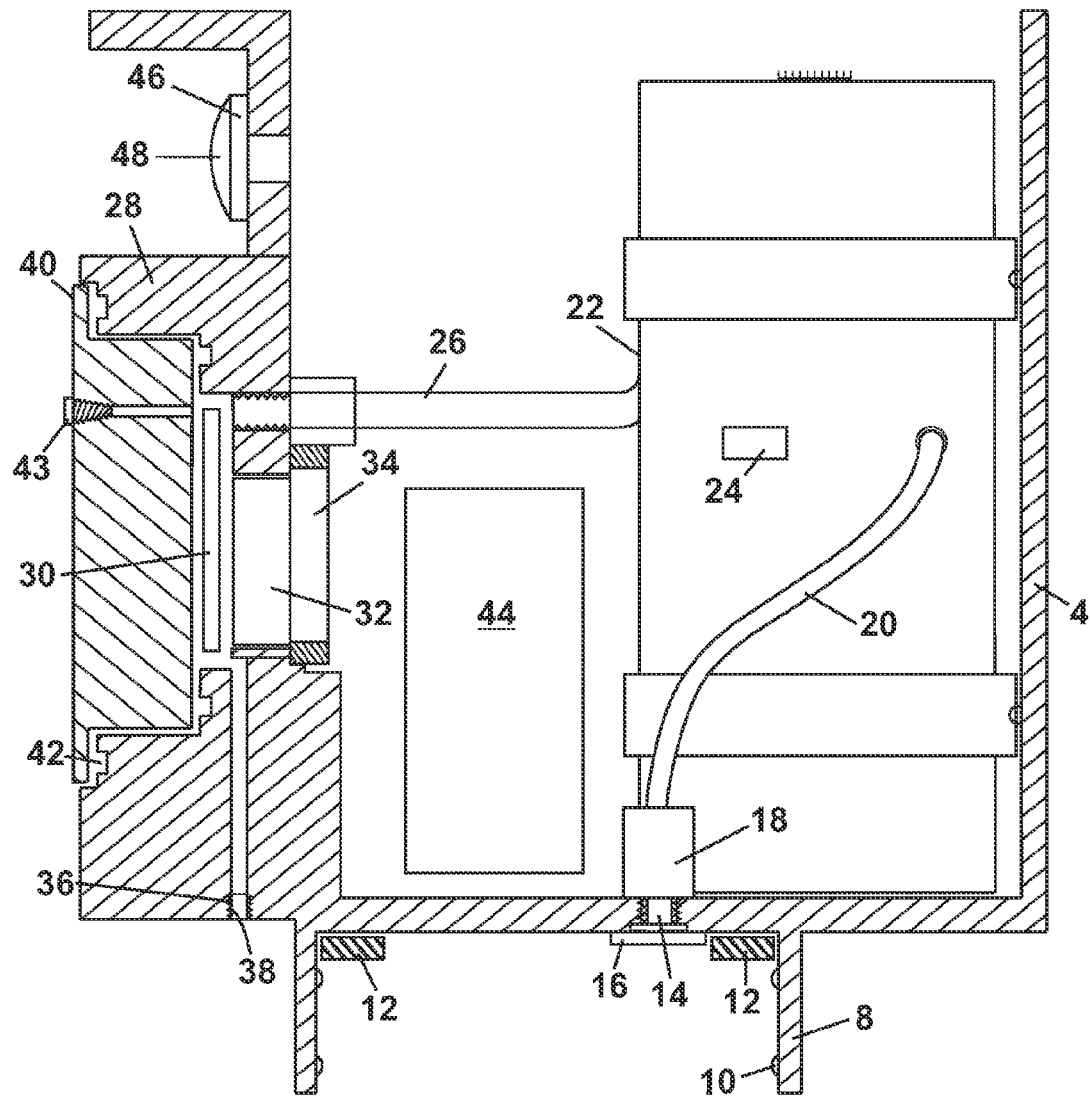
FIG. 2 is a vertically sectioned schematic illustration of the internal components of the apparatus shown in FIG. 1.
Figure 3:
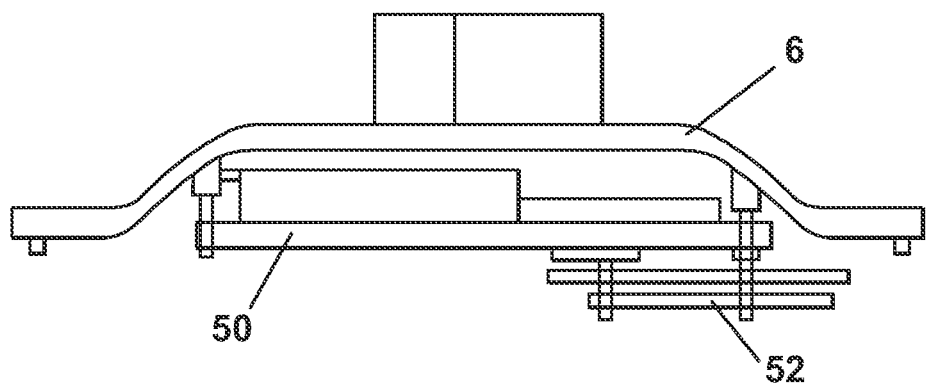
FIG. 3 is a vertically sectioned schematic illustration of the lid of the apparatus shown in FIGS. 1 and 2.
Figure 4:
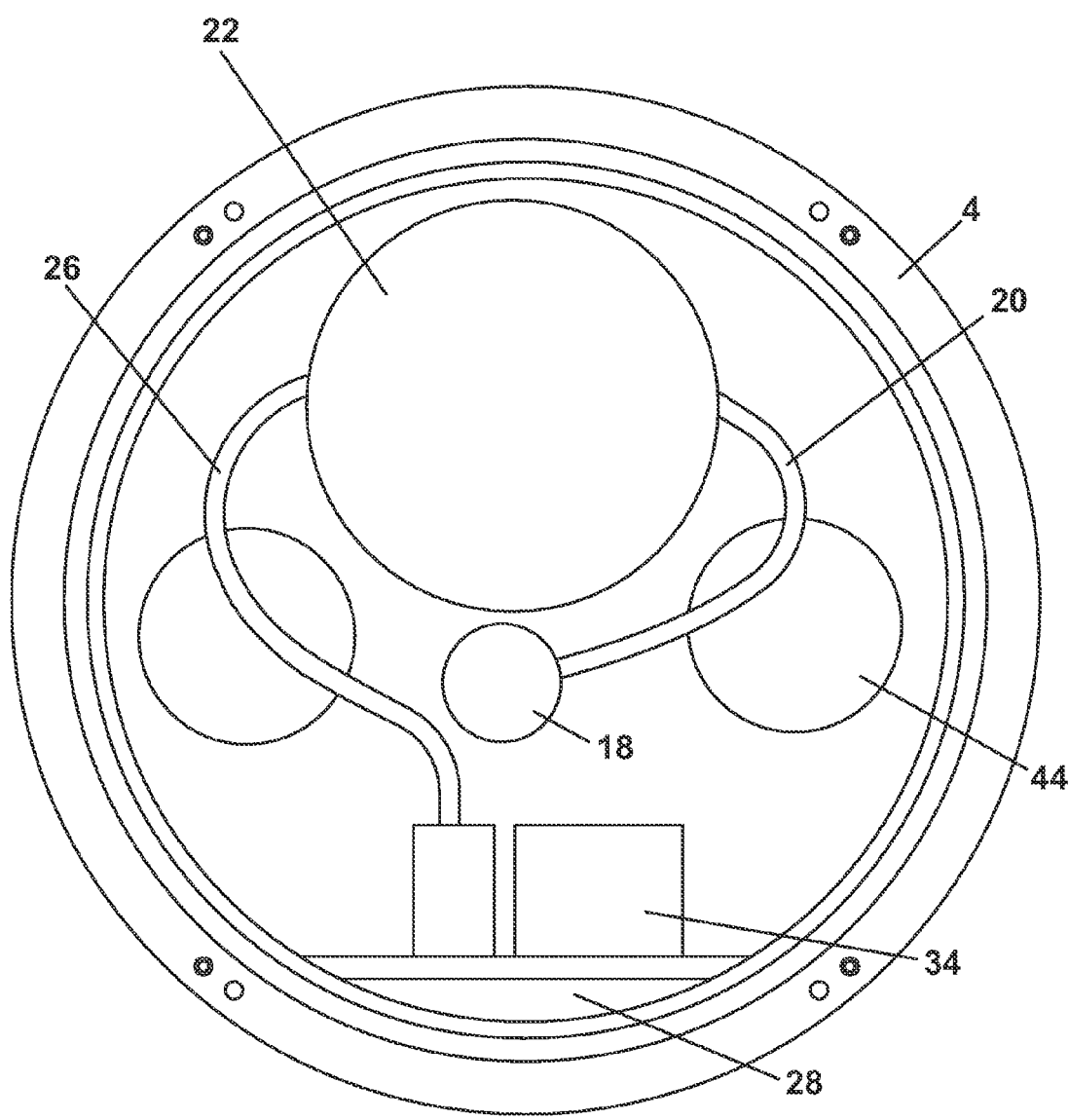
FIG. 4 is a schematic plan view of the apparatus shown in FIG. 2.

Referring to FIGS. 2-4 of the accompanying drawings, the sampling apparatus 2 further comprises an internal thread 10 on the hydrant connector 8 for connecting the apparatus 2 to a hydrant (not shown). An O-ring seal 12 helps form a watertight seal between the hydrant connector 8 and the hydrant.

From the hydrant connector 8 there is an inlet 14 carrying a filter 16 to prevent significant particulate material from entering the apparatus 2 that might block the flow pathway. A fitting 18 secures the filter 16 in place relative to the inlet 14. From the inlet 14, a flexible pipe 20 extends to a flow regulator 22 incorporating a non-return valve 24. A pipe fitting 26 extends from the flow regulator 22 to a sensor casing 28. In the sensor casing is provided a flow cell 30, a removable membrane 32 and a chlorine sensor 34. From the sensor casing 28, there is an outlet 36 including a threaded drain 38 so that the outflow may be directed to additional sensors or sampling devices.

A suitable flow regulator is a Micro-Flow available from WA Kates Company of 1363 Anderson, Clawson, Mich. 48017, USA. Excess fluid is vented from the apparatus.

The sensor casing 28 includes a cap 40 and O-ring seal 42 to enable access to the flow cell 30, removable membrane 32 and sensor 34. When the cap 40 is in place the flow cell 30 of known fixed volume and flow characteristics is formed between its inner face and the outer surface of the membrane 32. The cap 40 has a hole therethrough, normally filled by a removable threaded plug 43, through which calibration solutions can be pumped at known rates. Removal of the cap 40 permits the replacement of parts such as the membrane 32 to be carried out conveniently. The sensor 34 is configured to make chlorine level readings of water passing through the flow cell 30.

A suitable sensor is a CL4-1N available from Dr Reiss GmbH, Eisleber Str. 5, Weinheim, Germany.

The apparatus further comprises a battery 44, an RS232 connector 46 incorporating a button 48 to start and stop the device manually. The battery 44 powers the internal electronics of the apparatus 2.

In the lid 6 is located a GSM antenna 50 and a combined GSM/radio module and data logger 52 incorporating a memory.

A flow path through the apparatus 2 is provided from the inlet 14, to flexible pipe 20, flow regulator 22, pipe fitting 26, flow cell 30 to outlet 36.

In use, the assembled unit is attached to a water hydrant using the hydrant connector 8. The flow regulator 22, which can vary the flow rate through the apparatus, is configured so that there is a continuous flow, preferably a constant flow, of water through the apparatus 2. For hourly measurements of water quality, a preferred flow rate through the apparatus is 0.1 liters per minute. This is fast enough to ensure that the sensor is making a reading on a relatively current supply (i.e. the water being tested is substantially similar to that in the nearby pipe) whilst generating a sufficiently small volume of water that it is able to drain away without flooding the hydrant chamber.

Based on typical United Kingdom main distribution pressure, the pressure of the water incident on the sensor is less than 1 bar and preferably about 0.1 bar.

Periodically, say every hour, the sensor makes a reading of the chlorine level in the water and this information is stored in the memory of data logger 52. Either periodically, say daily or weekly, or when instructed to do so by a user, the apparatus downloads its data from the data logger 52. This can be wirelessly via the GSM/radio module 52 or by a physical connection to the RS232 port 46. Instructions to the apparatus 2 can be uploaded through these channels also, for instance to change the frequency of sampling.

Figure 5:
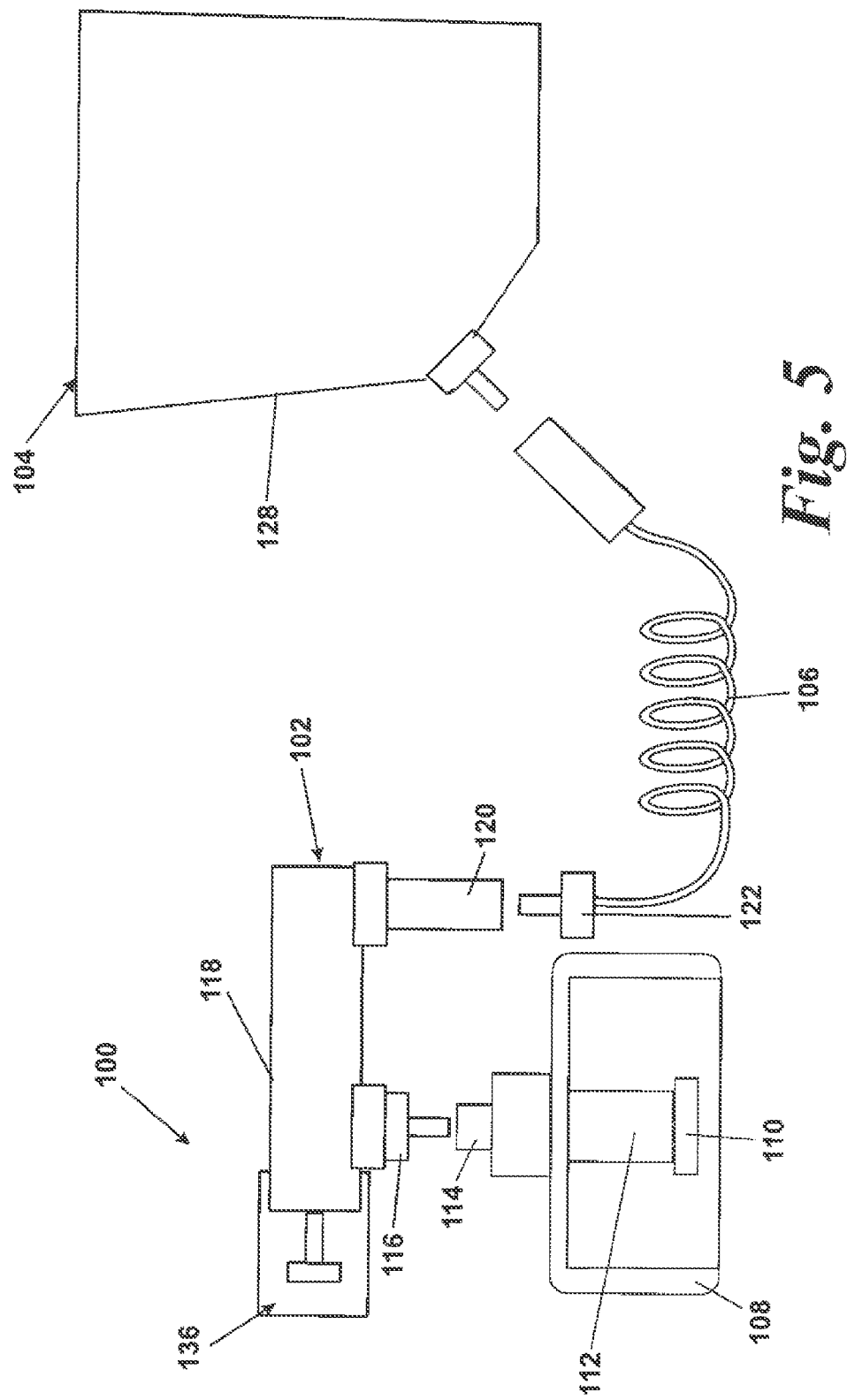
FIG. 5 is a schematic illustration of a sampling apparatus according to a second embodiment of the present invention.

Referring to FIG. 5 of the accompanying drawings, there is shown a sampling apparatus 100 comprising a first part 102 connected to a second part 104 by a flexible coil hose 106. First part 102 is for connection to a standard hydrant cap 108 and comprises, each in fluid communication with each other, a filter 110, a non-return valve 112, a female connector 114, a male connector 116, a flow regulator 118, a second female connector 120, a second male connector 122, which is connected to the flexible coil hose 106, in turn connected to a third female connector, a third male connector and a sensor unit 128.

Figure 6:
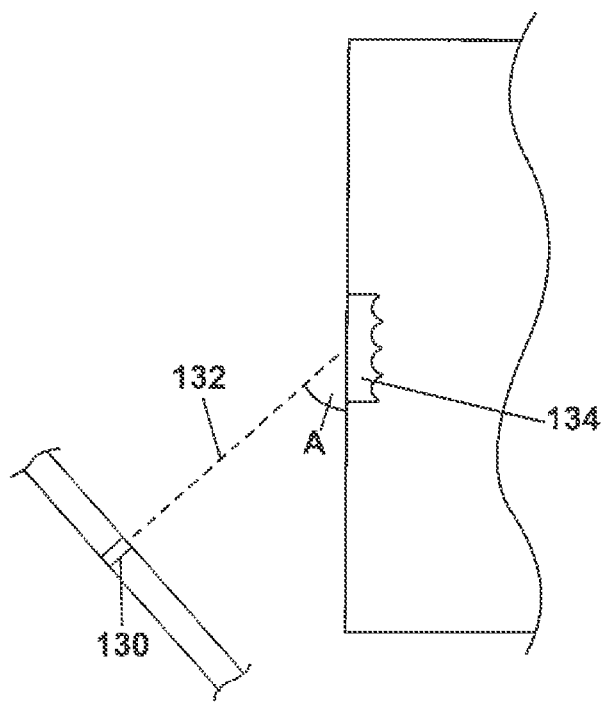
FIG. 6 is a schematic illustration of the sensor unit arrangement of the sampling apparatus of FIG. 5.

Referring to FIG. 6 of the accompanying drawings, an internal arrangement of the sensor unit 128 is illustrated. The sensor unit 128 comprises a hose outlet 130 as a fluid ejector directing a jet of fluid along the path indicated schematically by line 132 against a sensor 134. The sensor 134 is a chlorine sensor. It is noted that the outlet jet impinges on the sensor unit at an incident angle A, where A is approximately 45°. It has been found that by keeping this angle of incidence from 30° to 60°, the build up of bubbles and particulates on the sensor can be kept to a minimum.

The apparatus 100 can comprise an anti-tamper cover 136.

The second embodiment of the present invention can include the additional functionalities of the first embodiment of the present invention, such as an RS 232 interface, a GSM antenna and a data logger.

The first embodiment of the present invention can include features of the second embodiment, in particular the sensor arrangement.

The second embodiment, in use, operates similarly to the first embodiment of the present invention in that fluid flows continuously past the sensor 134.

The filter 110 helps keep particulates out of the apparatus.

By having the apparatus 100 in two parts 102, 104, it can more easily be fitted in a hydrant. It is noted that both embodiments of the present invention can be fitted within a hydrant container.

The male/female connectors enable the various components to push-fitted together.

The sensor 134 can be embodied in a removable and replaceable cartridge for easy maintenance.

The apparatus of the first and second embodiments of the invention is operated from the mains water pressure. This avoids the need for pumps.

By providing a continuous flow of fluid to the sensor, impinging on the sensor membrane, a reliable periodic reading can be taken. The continuous flow of fluid helps keep the sensor membrane clear of obstructions and reduces the need for moving parts in the apparatus.

The flow regulator provides that the fluid velocity is high enough to ensure adequate sensor response but also low enough to prevent damage that would otherwise be caused by mains pressure.

The chlorine sensor can be a chlorine residual sensor. In place of or in addition to the chlorine sensor 34 other sensors can be included in the apparatus 2, such as a pH sensor or an electrical conductivity sensor.

Although these embodiments of the present invention have been described in relation to the sampling of water, and is particularly intended for use in testing water in a water distribution system, referred to as a mains supply, further embodiments can be used for other liquids and even gases, i.e. fluids in general.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A sampling apparatus for sampling a liquid, the apparatus comprising a sensor and a flow regulator open to allow continuous flow of liquid through the apparatus from an inlet to an outlet via a fluid ejector past the sensor, wherein the fluid ejector is configured to direct liquid at the sensor at an incident angle of from 30° to 60°, in which the sensor is configured to periodically make a reading of a characteristic of the liquid so directed.

2. A sampling apparatus for sampling a liquid according to claim 1, wherein the apparatus is attachable to a hydrant.

3. A sampling apparatus for sampling a liquid according to claim 1, wherein the apparatus comprises a hydrant connector for connecting the apparatus to a hydrant, which hydrant connector comprises a threaded cap.

4. A sampling apparatus for sampling a liquid according to claim 1, wherein the reading is stored in a memory.

5. A sampling apparatus for sampling a liquid according to claim 1, wherein the apparatus comprises a connector for data download to an external device.

6. A sampling apparatus for sampling a liquid according to claim 1, wherein the apparatus further comprises a transmitter for the wireless transmission of data to an external device.

7. A sampling apparatus for sampling a liquid according to claim 1, wherein the sensor is selected from one of a chlorine sensor, a pH sensor and an electrical conductivity sensor.

8. A sampling apparatus for sampling a liquid according to claim 1, wherein the apparatus comprises a plurality of sensors selected from one or more of a chlorine sensor, a pH sensor and an electrical conductivity sensor.

9. A sampling apparatus for sampling a liquid according to claim 1, wherein the apparatus comprises a fluid flow path for liquid through the apparatus and a non-return valve in the fluid flow path.

10. A sampling apparatus for sampling a liquid according to claim 1, in which the flow regulator reduces the pressure of the liquid flow.

11. A sampling apparatus for sampling a liquid according to claim 1, wherein the incident angle is from 40° to 50°.

12. A sampling apparatus for sampling a liquid according to claim 1, wherein the sensor is a membrane sensor.

13. A sampling apparatus for sampling a liquid according to claim 1, wherein the flow rate through the apparatus is in the range 0.05 liters per minute to 3 liters per minute.

14. A sampling apparatus for sampling a liquid according to claim 13, wherein the flow range is from 0.05 liters per minute to 1 liter per minute.

15. A sampling apparatus for sampling a liquid according to claim 13, wherein the flow rate is in the range 0.075 liters per minute to 0.5 liters per minute.

16. A sampling apparatus for sampling a liquid according to claim 13, wherein the flow rate is in the range 0.09 liters per minute to 0.15 liters per minute.

17. A sampling apparatus for sampling a liquid according to claim 13, wherein the flow rate is 0.1 liters per minute.

18. A sampling apparatus for sampling a liquid according to claim 1, wherein the liquid is water.

19. A sampling apparatus for sampling a liquid according to claim 1, wherein the apparatus is for sampling water in a water distribution network.

20. A sampling apparatus for sampling a liquid according to claim 19, wherein the apparatus is configured whereby the water pressure is from the mains supply.

21. A method of operating an apparatus according to claim 1, which the method comprises, when the apparatus is attached to a liquid supply configuring the flow regulator to all the continuous flow of liquid through the apparatus.

* * * * *